United States Patent [19]
Stouffer et al.

[11] Patent Number: 5,140,988
[45] Date of Patent: Aug. 25, 1992

[54] DETECTION OF ABNORMAL BONE STRUCTURE IN ANIMALS AND CARCASSES WITH ULTRASOUND

[75] Inventors: James R. Stouffer, Ithaca, N.Y.; Dale C. Miller, Apex, N.C.; Yujun Liu, Ithaca, N.Y.

[73] Assignee: Animal Ultrasound Services, Inc., Ithaca, N.Y.

[21] Appl. No.: 748,503

[22] Filed: Aug. 22, 1991

[51] Int. Cl.⁵ .............................................. A61B 8/00
[52] U.S. Cl. .......................... 128/660.01; 128/660.07; 73/861.25
[58] Field of Search ...................... 128/660.01, 660.07, 128/702; 73/629, 861.25

[56] References Cited

U.S. PATENT DOCUMENTS

| | | | |
|---|---|---|---|
| 3,496,764 | 2/1970 | Stouffer | 128/660.07 |
| 3,603,303 | 9/1971 | Stouffer | 128/660.01 |
| 4,099,420 | 7/1978 | Stouffer et al. | 73/629 |
| 4,359,055 | 11/1982 | Carlson | 128/661.03 |
| 4,359,056 | 11/1982 | Carlson | 128/661.03 |
| 4,448,200 | 5/1984 | Brooks et al. | 128/660.01 |
| 4,742,458 | 5/1988 | Nathans et al. | 128/702 |
| 4,785,817 | 11/1988 | Stouffer | 128/660.07 |
| 4,949,312 | 8/1990 | Iwasawa | 128/660.01 |
| 4,976,267 | 12/1990 | Jeffcott et al. | 128/660.01 |
| 5,060,515 | 10/1991 | Kanda et al. | 128/660.01 |

OTHER PUBLICATIONS

Muscle Metabolism and Real-Time Ultrasound Measurement of Muscle and Subcutaneous Adipose Tissue Growth in Lambs Fed Diets Containing a Beta-Agonist—Stouffer et al—J. Anim. Sci. 1986, 63:1410–1417.
Estimating Fatness in Horses and Ponies—Stouffer et al., Jour. Anim. Sci., vol. 43, No. 4 (1976).
Syllabus—2nd Annual AIUM Animal Ultrasound Seminar & Wet-Lab, American Institute of Ultrasound in Medicine—1990.
The Use of Ultrasound to Predict the Carcass Composition of Live Cattle—A Review—Animals Breeding Abstracts—G. Simm, vol. 51, No. 12, 1983.
Ultrasonic Determination of Body Composition—J. R. Stouffer, Dec. 1968.
Studies on the Pathogenesis of Staphylococcal Osteomyelitis in Chickens—I. Effect of Stress on Experimentally Induced Osteomyelitis, Mutalib et al—Avian Dis., vol. 27, No. 1, Jan.-Mar. 1983, pp. 141–156.
Ultrasonics of Postmortem Detection of Animal Diseases and Abnormalities—J. R. Stouffer—Seminar for FSIS-USDA—Sep. 18, 1985.
Die Anwendung non Ultraschallmessungen in den USA—J. R. Stouffer, pp. 64–70.
Real Time Ultrasound Evaluation—J. R. Stouffer—Jun. 1988.
Relationships of Empty-Body Composition and Fat Distribution to Live Animal and Carcass Measurements in Bos Indicus-Bos Taurus Crossbred Cows—Holloway et al—pp. 1818–1826.

(List continued on next page.)

Primary Examiner—Francis Jaworski
Assistant Examiner—George Manuel
Attorney, Agent, or Firm—Ralph R. Barnard

[57] ABSTRACT

Method and apparatus for determining a condemnation condition in a post mortem animal intended for human consumption is taught hereinabove. The apparatus includes an ultrasound machine, including a probe, wherein the probe is positioned on the animal such that a cross-sectional image of the portion of the animal to be examined is shown. An image analyzer determines and identifies a pattern of anatomically distinct tissue and bone outline of the animal shown on the image. Pattern recognition equipment compares the pattern of tissue and bone outline with a norm reference for a healthy animal and at least one known deformation pattern for tissue of animals requiring condemnation. If a greater correlation with one of the known deformation patterns than with the norm reference pattern is shown then, means for indicating a condemnation condition for the animal are activated. Also taught hereinabove, is a method of developing further tests for determining a condemnation condition in an animal.

14 Claims, 8 Drawing Sheets

OTHER PUBLICATIONS

Ultrasonics for Live Lamb and Carcass Evaluation, J. R. Stouffer, 1988 Proceeding Sheep Industry Development Program, Denver, Colo.

Syllabus—Animal Ultrasound Seminar & Wet-Lab—Oct. 13-15, 1989.

Ultrasonographic Evaluation of the Urinary System and Prostate Gland in the Dog and Cat—R. Badertscher—Veterinary Imaging Professional.

Meat and Poultry Inspection—National Academy Press—1985.

Tendon and Ligament Ultrasound in the Equine Athlete—A. Kent Allen—Allen-Schneider Equine Hospital.

A Review of Potential New Methods of On-Line Pork Carcass Evaluation—Forrest et al—J. Anim. Sci 1989—67:2164-2170.

A Review of Ultrasonic Applications in Animal Science—J. R. Stouffer—Journal of Clinical Ultrasound—vol. 5, Apr. 1977.

Ultrasound for Animal Evaluation—J. R. Stouffer—New York's Food and Life Sciences—vol. 10, No. 3, 1977.

Objective Technical Methods for Determining Carcass Value in Live Animals with Special Emphasis on Ultrasonics—J. R. Stouffer—World Review of Animal Production—1966.

Mild Exercise—Effect on Body Composition and Metabolism, Stouffer et al—N.Y. State Journal of Med.—Aug. 1974.

Relationship of Ultrasonic Measurements and X-Rays to Body Composition—J. R. Stouffer—Annals of the N.Y. Academy of Sci, vol. 110, Part I. pp. 31-39—Sep. 1963.

Ultrasonics for Evaluation of Live Animal and Carcass Composition—J. R. Stouffer—Twelfth Research Conference—pp. 81-87.

Development and Application of Ultrasonic Methods for Measuring Fat Thickness and Rib-Eye Area in Cattle and Hogs—J. R. Stouffer et al—Journal of Animal Sci., vol. 20, No. 4, Nov. 1961.

Ultrasonic News—Winter 1960—vol. IV No. 4.

Comparison of Methods Used for Carcass Evaluation in Swine, Doornenbal et al—Jou. of Ani. Sci., vol. 21, No. 3, Aug. 1962.

Techniques for the Estimation of the Composition of Meat Animals—J. R. Stouffer, pp. 207-219.

Status of the Application of Ultrasonics in Meat Animal Evaluation—J. R. Stouffer—pp. 161-173.

Ultrasonic Research in Europe—J. R. Stouffer—Mar.-Aug. 1962.

The Ultrasonic Approach to Measuring Fat and Muscling in Live Beef Cattle—J. R. Stouffer—pp. 34-35.

Carcass Evaluation and Its Research Applications—J. R. Stouffer—1961—pp. 32-36.

Application of Ultrasound in the Livestock and Meat Industry, J. R. Stouffer—pp. 310-315.

Meat Evaluation in Live Animals—J. R. Stouffer—Frontiers in Food Research, Cornell University, Apr. 12-13, 1966, pp. 102-108.

DETECTION OF ABNORMAL BONE STRUCTURE IN ANIMALS AND CARCASSES WITH ULTRASOUND

FIELD OF THE INVENTION

The present invention relates to methods and apparatus for determining abnormal tissue and bone formation in animals, and more particularly relates to methods and apparatus for determining abnormal tissue and bone formation in animals using ultrasound.

BACKGROUND OF THE INVENTION

Many different types of evaluations are carried out on meat products before they are approved for commercial sale. Some of these procedures involve a system of grading depending upon fat and muscle content and distribution, while others involve condemnation decisions.

Various types of ultrasonic apparatus for examining the internal structure of humans and animals are, of course, well known in the prior art. The use of ultrasonic techniques for inspecting live animals for fat thickness has long been proposed, particularly in percentage of fat, so that the fat indication provides a reasonable indication of carcass composition.

The advantage of using ultrasonic apparatus to inspect and grade livestock are numerous. Primarily, an animal's value can be assessed prior to death, which can be very important for herd evaluation and selection of breeding stock. After the initial investment in the equipment, the process of livestock evaluation, is quick and inexpensive and in no way harms the animal because the ultrasonic waves are not damaging and do not require expensive film developing procedures as with X-ray.

A grading determination is based upon the relative quantity of fat or muscle within a normal set of parameters. The normal set of parameters are the same for each animal within a particular species (e.g. the number of fat or muscle layers) whereas the proportion each type of tissue within these parameters differs for each individual animal. Ultrasound techniques have been used extensively to determine grading characteristics of livestock.

A condemnation or sorting decision involves comparing each animal against a norm reference for its particular species and condemning (—eliminating from the food supply) any animals showing any abnormal conditions indicative of disease or other health related problems. Quantity of the abnormality is generally not a factor, but rather its presence or absence is enough. Heretofore, ultrasound technology has not been used in the condemnation sorting decision made by meat inspectors.

Many abnormalities that require condemnation affect the skeletal structure of animals. While ultrasonic apparatus and methods have been used extensively to evaluate and characterize tissue and conditions causing tissue damage, ultrasound technology has not been used to characterize or evaluate bone structure. Ultrasonic waves do not pass through bone, therefore the only image presented is an outline of the bone rather than a cross-sectional image as is shown of other tissues (e.g. muscle and fat layers).

Many post mortem inspection processes involve first inspecting a whole carcass to look for suspected problems, and actually cutting into a suspected infected animal to further evaluate the amount of damage. Often the animal turns out to be healthy, but has still been significantly reduced in value because of the disruption of an otherwise whole animal part. One such inspection that is carried out, is an inspection for osteomyelitis. Osteomyelitis is a bone disorder in poultry resulting from Staphylococcal auerus infection which is the primary cause of food poisoning in humans eating poultry. Osteomyelitis is discussed in "Studies on the pathogenesis of staphylococcal osteomyelitis in chickens,—I. Effect of Stress on Experimentally Induced Osteomyelitis", by Mutalib et al—Avian Dis., Vol. 27, No. 1, January-March 1983 pg 141-156, incorporated herein by reference.

Long bones, e.g. tibia, which are infected by Staphylococcal auerus become inflamed and enlarged (osteomyelitis) and the Staph. auerus may be transmissible to humans. Currently Federal Meat Inspectors cut soft tissue and bones of possibly inflamed tibia at the femur joints to observe the marrow. On average only 10% of the cut carcasses are diseased, which means the industry is losing enormous amounts of money on the 90% of otherwise healthy poultry by using this method of inspection.

Using X-ray equipment to analyze conditions affecting the bone structure of an animal is impractical and expensive. The industry is in need of an inspection technique for osteomyelitis that does not require the cutting of so many healthy poultry falsely suspected of infection.

SUMMARY OF THE INVENTION

It is a primary objective of this invention to provide a new and improved apparatus and method for detecting abnormalities in bone formation of animals intended for human consumption.

It is a further objective of this invention to provide a new and improved apparatus and method for determining a condemnation condition in a post mortem animal intended for human consumption.

It is a further objective of this invention to provide a new and improved apparatus and method for determining a bone deformation condition in a post mortem animal intended for human consumption.

It is a further objective of this invention to provide a new and improved method of developing a test for determining a condemnation condition in a post mortem animal intended for human consumption.

One discovery of the present invention is that ultrasound technology can be used to detect a bone deformation condition. Heretofore, ultrasound has not been used to image bone conditions because only the outline of the bone structure is provided. By correct placement of an ultrasonic transducer and interpretation of the outline image of the bone, bone deformation conditions can be discovered without using X-ray equipment or having to cut into the meat of an animal.

The method of determining a bone deformation condition in an animal taught by the present invention includes positioning an ultrasonic probe on the animal such that a cross-sectional image is shown which includes an outline of a portion of bone to be examined. The image of the bone outline is compared with a norm reference image of a bone outline for a healthy animal and at least one known deformation pattern of images of bone outlines for animals requiring condemnation. The animal is condemned if the image has a greater correlation with one of the known deformation patterns than with the norm reference pattern.

A method of determining a condemnation condition in a post mortem animal intended for human consumption is taught hereinabove. The method includes positioning an ultrasonic probe on the animal such that a cross-sectional image is shown. The image is compared with a norm reference pattern and at least one known deformation pattern for tissue for animals requiring condemnation. The animal is condemned if the image has a greater correlation with one of the known deformation patterns than with the norm reference pattern. The correlation measurements and comparison can be performed by an image analyzer and pattern recognition equipment modified to recognize the known deformation patterns such that the condemnation decision is made automatically by a machine. Also taught hereinabove, is a method of developing further tests for determining a condemnation condition in an animal.

The teachings of the present invention include, an apparatus for determining a condemnation condition in a post mortem animal intended for human consumption. The apparatus includes an ultrasound machine, including a probe, wherein the probe is positioned on the animal such that a cross-sectional image of the portion of the animal to be examined is shown. Pattern recognition equipment determines and identifies a pattern of anatomically distinct tissue and bone formation of the animal shown on the image. An image analyzer compares the pattern of tissue and bone formation with a norm reference for a healthy animal and at least one known deformation pattern for tissue of animals requiring condemnation. If a greater correlation with one of the known deformation patterns than with the norm reference pattern is shown then, means for indicating a condemnation condition for the animal are activated.

The methods and apparatus of the present invention are used for poultry by comparing the outine of a bone image with a known deformation pattern of a deformed medial condyle of an animal having a condition causing osteomyelitis. Heretofore, no method or apparatus used in conjunction with ultrasound technology taught the indication of a condemnation condition in meat inspection.

These and other objects, features and advantages of the present invention should become apparent from the following description when taken in conjunction with the accompanying drawings.

DETAILED DESCRIPTION OF THE PREFERRED EMBODIMENT

Figure 1:
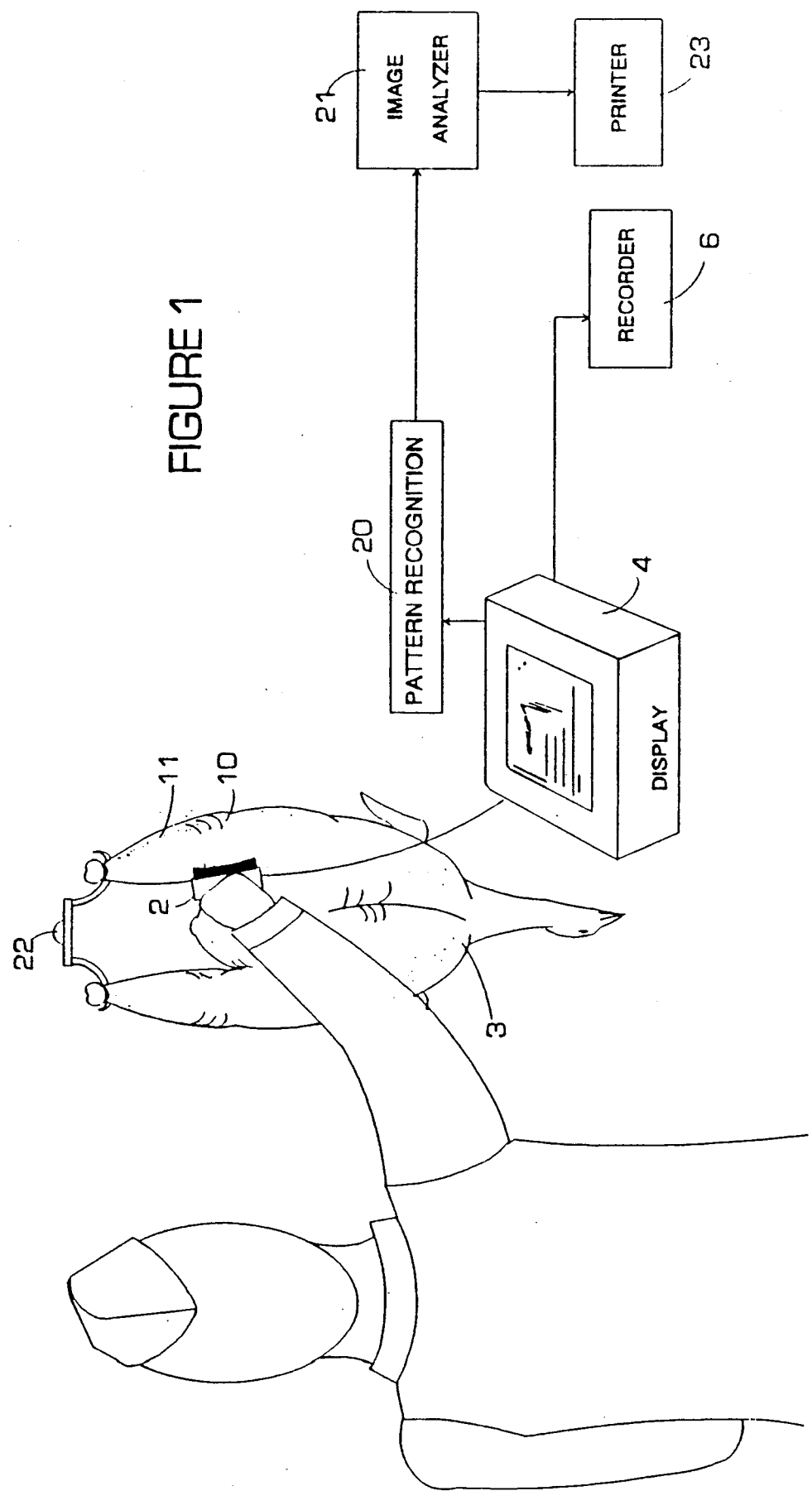
FIG. 1 is a perspective view of an individual positioning an ultrasonic probe on a poultry carcass.

For the purposes of promoting an understanding of the teachings of the present invention, references will now be made to the embodiments illustrated in the drawings and specific language will be used to describe these embodiments. It will nevertheless be understood that no limitation of the scope of the invention is thereby intended, alterations and further applications of the teachings of the present invention as illustrated and described hereinabove is anticipated by those skilled in this art.

Referring now to FIGS. 1–6, the method and apparatus are shown in various embodiments. FIG. 1 is a perspective view of an individual using an ultrasound inspection station 1 as taught by the present invention. The inspector is positioning an ultrasonic probe 2 on a turkey carcass 3. The inspection station 1 includes an ultrasonic scanner and monitor 4, attached to the probe 2 for transmitting and receiving ultrasound signals, the probe is positioned on the carcass 3 such that a cross-sectional image of the portion of the animal being examined is shown on the display 5. This can be connected to a recorder apparatus 6 for recording these images for later analysis or use in creating a reference pool.

After the inspector positions the ultrasonic transducer probe 2 on the carcass 3 such that the cross-sectional image is shown on the display, the image on the display 5 is compared with a norm reference for a healthy animal and at least one known deformation pattern for tissue for animals requiring condemnation. These reference patterns can be provided by computer generated images by combining pools of image scans, image printouts, or the experience and knowledge of a trained veteran ultrasound inspector (i.e. knowing what to look for). The carcass 3 is condemned if the image on the display 5 has a greater correlation with one of the known deformation patterns than with the norm reference pattern. Some deformation patterns will show up as glaring abnormalities in relative tissue images, such as tumors, abscesses, etc. One such example, is the deformation pattern caused by osteomyelitis in poultry as taught hereinabove.

Figure 2A:
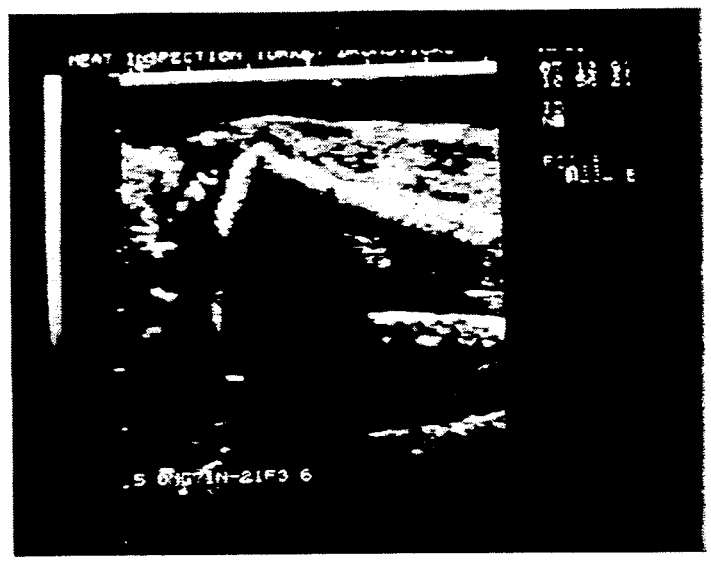
FIGS. 2a and 2b are photographs of ultrasonic images of healthy turkey drumsticks.
Figure 2B:
Figure 3A:
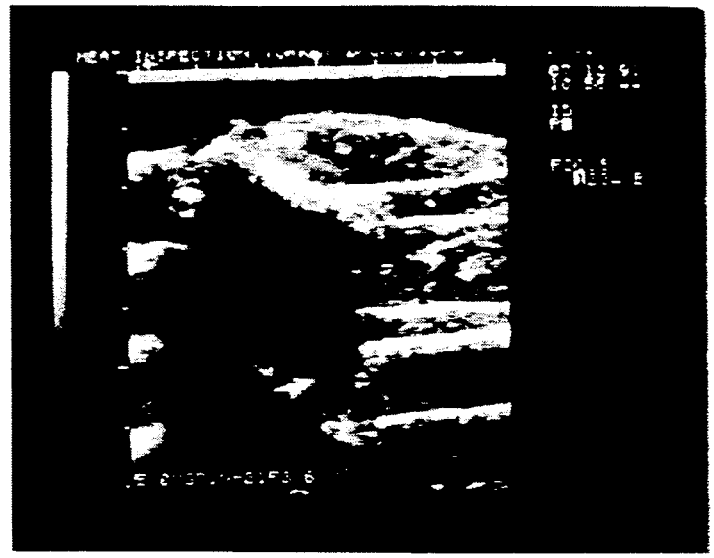
FIGS. 3a and 3b are photographs of ultrasonic images of turkey drumsticks which have osteomyelitis.
Figure 3B:

Osteomyelitis is a bone disorder in poultry which is indicative of an infection from Staphylococcal auerus. Staph. auerus is the primary cause of food poisoning in humans. The infection causes necrotic lesions of the bone which shows up on the bone outline image as a rounding of the tip of the medial condyle. As shown in FIGS. 2a and 2b, ultrasonic images of healthy turkey drumsticks show a sharp edge on the bone shadow image of the tip of the medial condyle (see FIG. 4 for location of the medial condyle 18). As shown in FIGS. 3a and 3b, ultrasonic images of turkey drumsticks which have osteomyelitis have a deformed medial condyle as can be seen by the notably rounded tip.

Figure 4A:
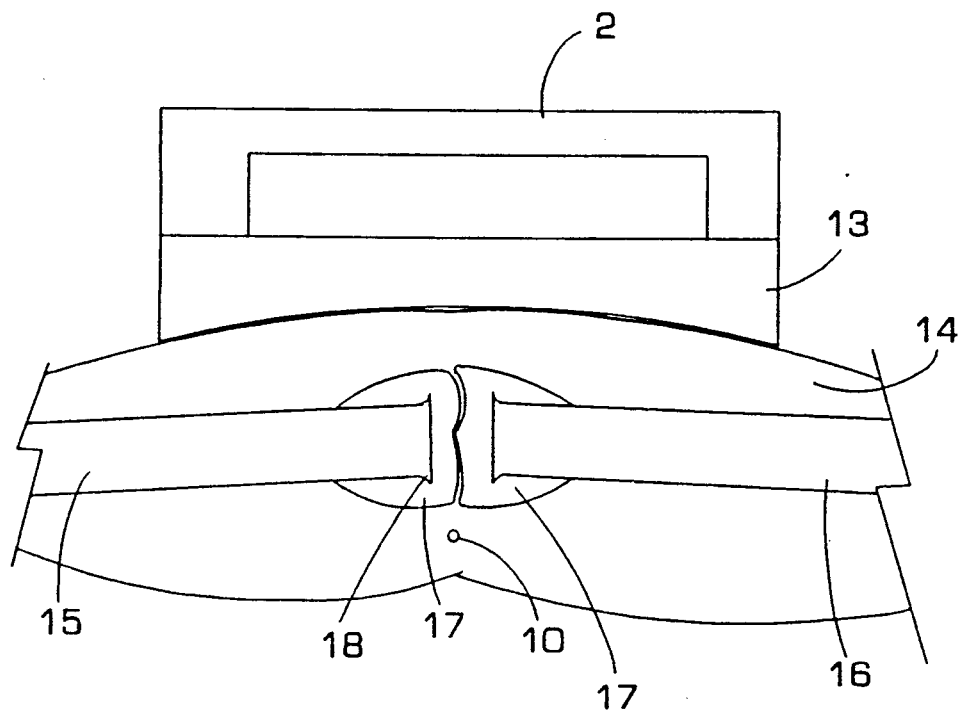
FIGS. 4a and 4b are a cross-sectional and a top view of a poultry leg showing proper positioning of an ultrasonic probe.
Figure 4B:
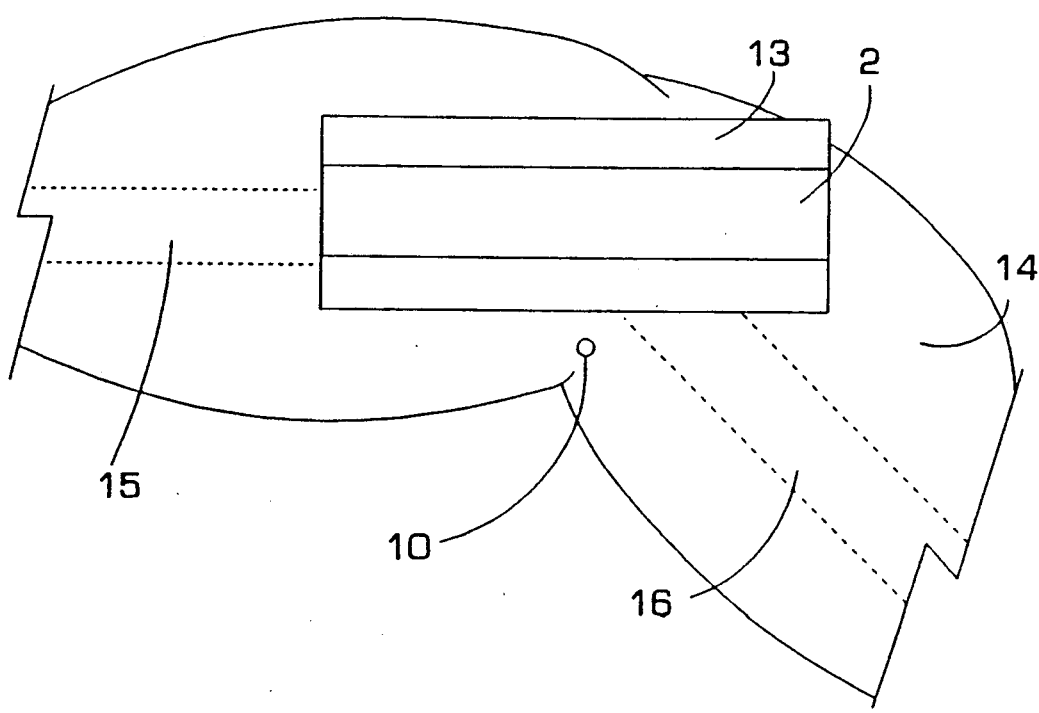

As shown in FIG. 4b, making contact of the leg tissues over the tibia-femur joint 10 with an ultrasonic transducer probe 2 provides a real time (15×second) image that shows minor change due to inflammation. This osteomyelitis condition is detected using ultrasound, which does not require the carcasses to be cut open, thereby providing industry with savings in product value and labor. A linear or convex transducer array probe 2 is placed over the tibia-femur joint 10 (being sure that the tissue to probe surfaces are moist, i.e. adequate couplant). The direction and orientation of the probe 2 are critical for a good image. This image is displayed on the display 5 and shows the bone characteristics.

As stated previously, the direction and orientation of the probe 2 on the carcass 3 are critical for a good image. FIG. 4 is a cross-sectional view of a poultry leg 11 showing proper positioning of an ultrasonic probe 2. The probe 2 includes a standoff gel 13 which is flexible to allow unbroken contact with the tissue 14. This standoff gel is generally made of a polyvinyl chloride gel with a resin additive. Superflab TM and Flexgel TM are both types of gels used for this purpose. The gel 13 is slightly curved for good contact with the curved tissue 14. In an assembly line application, gels 13 could be shaped to insure uniform and accurate positioning. The gel 13 would be molded to fit into the joint 10 between the leg and the thigh.

Adequate couplant fluid must also be used to insure that there is no air between the standoff gel 13 and the tissue 14. Water is an adequate couplant fluid for examining poultry with ultrasound. The carcasses 3 could be already wet from other processing or could be automatically moistened before examination. The joint 10 between the tibia 15 and the femur 16 is shown. Most consumers recognize the cartilage 17 surrounding the ends of the bones 15 and 16, however, the actual tip of the medial condyle 18 is under the cartilage 17. By positioning the probe 2 over the midline of the medial plane of this joint 10, the medial condyle tip 18 can be seen clearly.

Experienced ultrasound technologists will be able to position a probe 2 to achieve the desired image cross-section, by once they know to look for the bone outline as taught by the present invention. One positioning tip is that there is usually a tendon running directly across one of the better positioning planes, however, proper positioning will differ somewhat for each bird.

The inspector can use a linear (image shown in FIGS. 2a and 3a) or convex (image shown in FIGS. 2b and 3b) transducer probe 2. The inspector examines the medial condyle tip 18 without having to damage the carcass 3 in any way. Any ultrasound capable of producing at least a cross-sectional image could be used. One specific ultrasound machine that could be used to practice the teachings of the present invention is the Aloka 500 V with transducer probe UST 588-5 or UST 932-7.5; a brochure for this model is incorporated herein by reference. The specific frequency (i.e. 5.0 or 7.5, etc.) used is also a matter of choice, depending on the depth of the image desired and the amount of clarity needed. The specific inspection method taught hereinabove, can be easily detected with deep probing frequencies which are generally less clear, yet the bone portion to be examined is relatively near the surface such that less deeply probing frequencies can be used if greater clarity is desired.

The inspector interprets the image or a pattern recognition system 20 could be operatively connected to the display 5. The pattern recognition system 20 could also be connected to an image analyzer 21 which would automatically identify normal or abnormal tissue. The pattern recognition equipment 20 identifies patterns of anatomically distinct tissue and bone formation of the carcass 3 shown on the image. The image analyzer 21 compares the pattern of tissue and bone formation with a norm reference for a healthy animal and at least one known deformation pattern for tissue for animals requiring condemnation. One system that could be programmed to handle the image analysis is an AniMorph image analyzer. The pattern recognition equipment 20 and the image analyzer 21 could physically be incorporated into a single piece of equipment, however, each function must be performed. The pattern recognition equipment 20 selects appropriate portions of the image for analysis and the image analyzer 21 analyzes the selected portions of the image.

The pattern recognition equipment 20 and image analyzer 21 calculate a pattern of tissue and bone formation of the carcass 3 being examined. If there is a greater correlation with one of the known deformation patterns than with the norm reference pattern, the animal is condemned. This can be done by activating means for indicating a condemnation condition for the carcass 3, for example a light 22. This condemnation condition can be indicated in many different ways including electrical or mechanical signals, and the physical removal of the carcass 3 from the processing line. In all situations, there is an eventual separation of the condemned carcasses from the healthy carcasses. Heretofore, no method or apparatus used in conjunction with ultrasound technology taught the indication of a condemnation condition in meat inspection.

The pattern recognition software for selecting bone image portions would be relatively simple because the bone casts a shadow over the rest of the image, so the last line on the display is going to be the outline of the bone. Once the bone outline is determined, comparing the proportional bone curve to a set of curvature proportions for healthy and unhealthy birds is simple statistical calculation. The printer 23 could be used to provide periodic reports of the number of carcasses examined, number condemned, hourly rate of examination, etc.

Figure 5A:
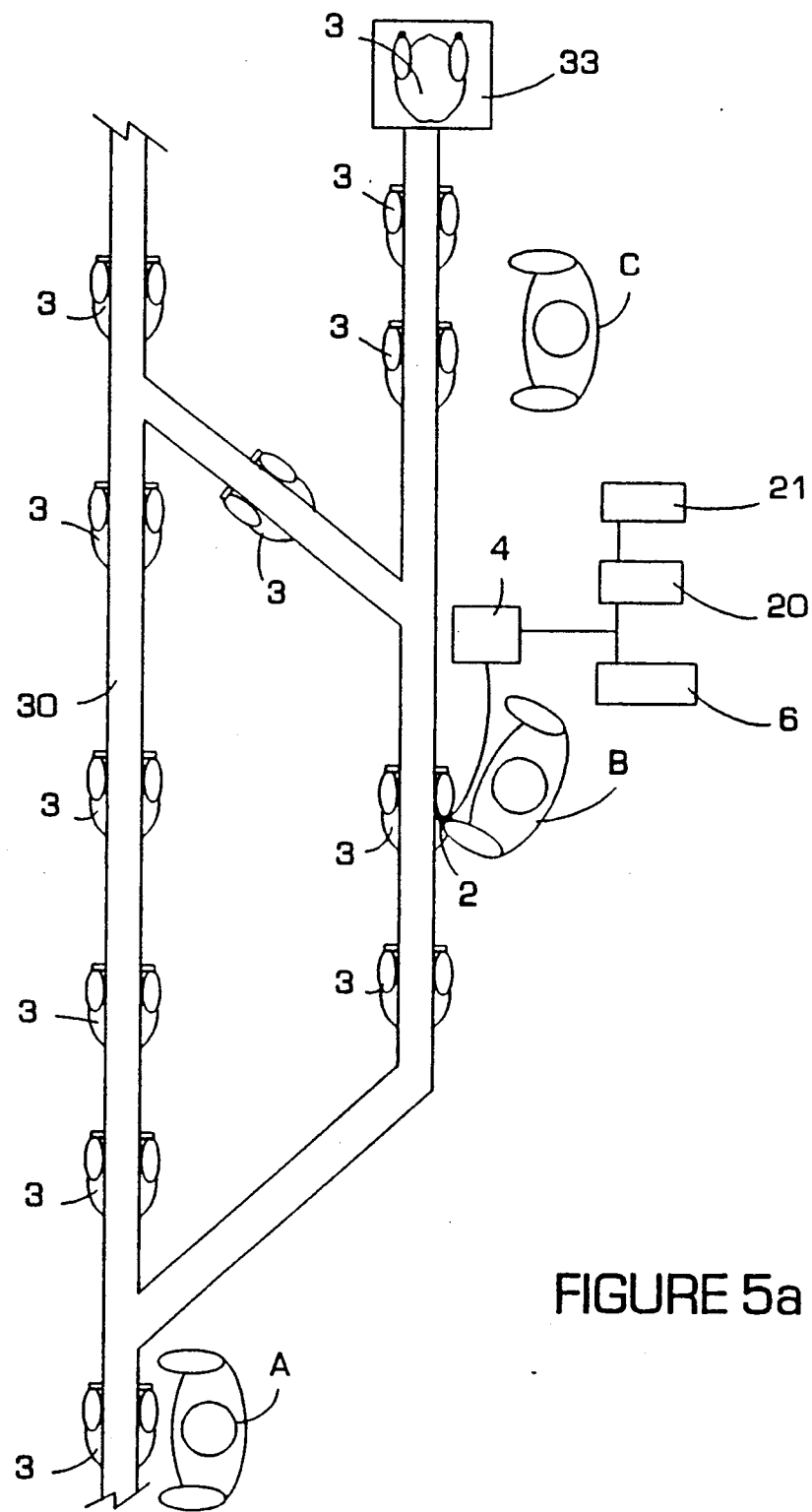
FIGS. 5a-c are perspective views of inspectors implementing the apparatus and methods taught by the present invention to inspect poultry carcasses at different positions on an assembly line.

FIG. 5a shows one possible implementation of the apparatus and methods taught by the present invention in the inspection of poultry carcasses on an assembly line. The poultry carcasses 3 are on a main assembly line 30 and an inspector A quickly inspects each one for joint inflammation and transfer any suspect carcasses to a side track 31. A second inspector B then inspects each carcass using ultrasound equipment 4. Any diseased carcasses are sent down a condemnation track 32 to a waste bin 33 for disposal or to have the diseased positions cut out by an inspector C. This is the preferred embodiment in the initial implementation of the teachings of the present invention because the inspector C could double check the condemnation decision of the machine until confidence in the system developed. In this embodiment the means for indicating a condemnation condition is the positioning of the carcasses on the condemnation track 32. After inspection of suspect carcasses on side track 31 any healthy carcasses would be reintroduced on the main track 30 for further processing. The primary advantage of using a side track 31 for ultrasound inspection is that the sight examination might initially take less time and more carcasses could be processed by only using ultrasound to inspect suspect carcasses.

Figure 5B:
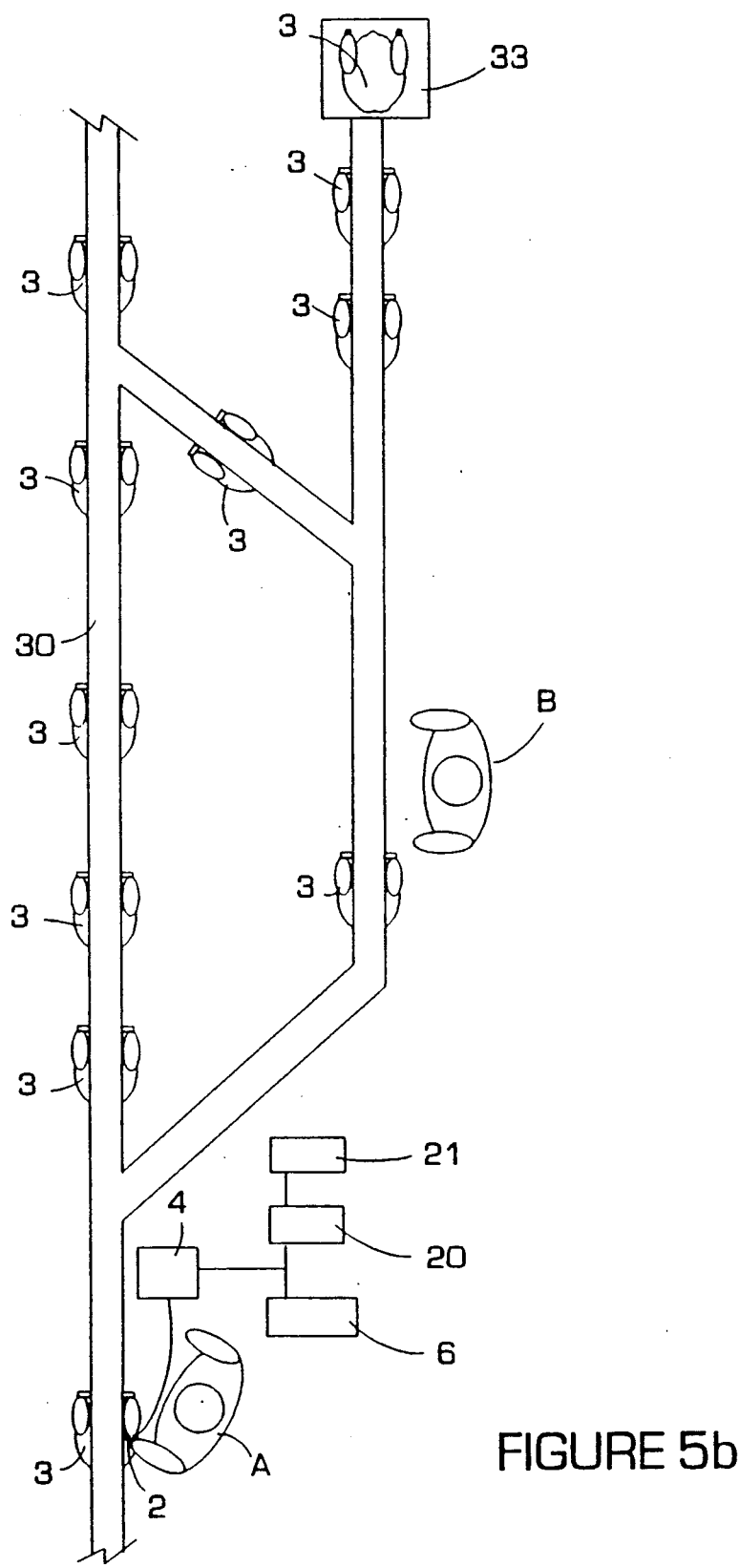

FIG. 5b shows an inspection system where an inspector A is making an initial condemnation determination by positioning the carcasses on the side track 31. A second inspector then inspects the carcasses 3 by cutting them open and making the final determination decision. This embodiment is advantageous in that two human inspectors make the condemnation determinations, however, the initial determination by inspector A does not turn up so many falsely suspect poultry so the processing can be increase greatly. Overall, fewer inspectors at station B are needed because the work load for this station is cut by about 80-90%, when compared to the current method of inspection.

Figure 5C:
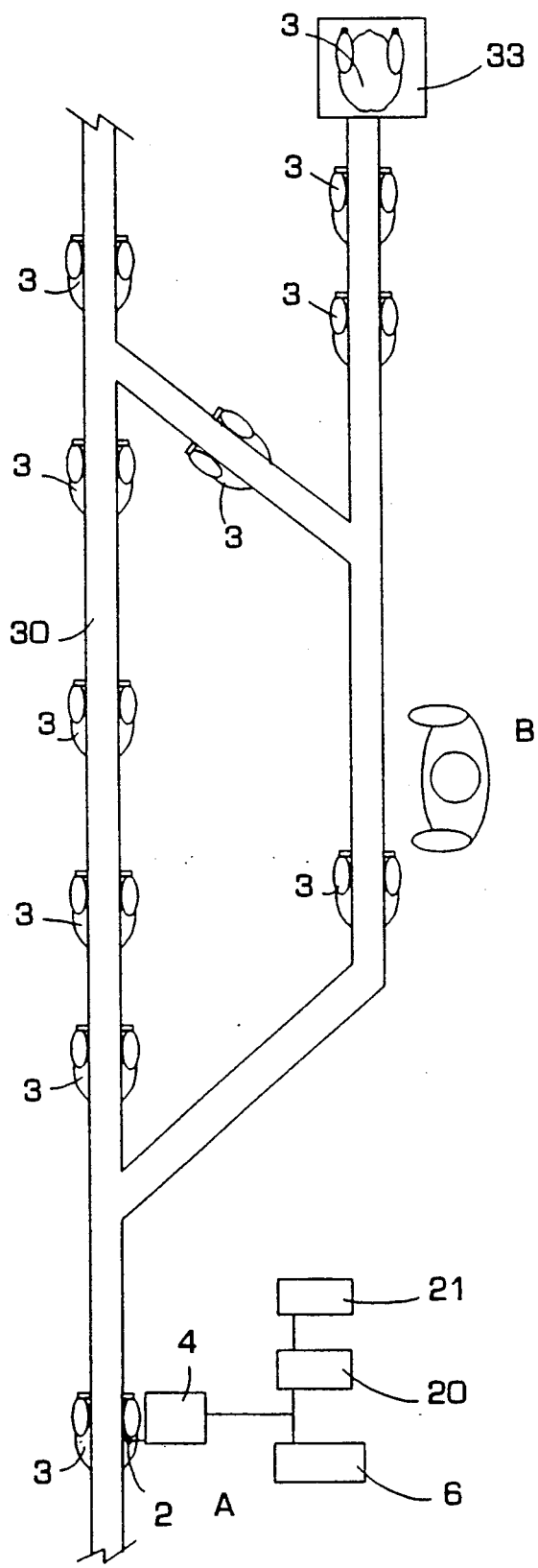

FIG. 5c shows one possible embodiment of an automated ultrasound inspection station, wherein the ultrasound probe 2 is positioned automatically. The machine at inspection A would make the initial condemnation decision and place the carcasses 3 on a track 31 for further inspection and cutting by an inspector B. While each station shows an inspector subsequent to an ultrasound station, this is not intended as a limitation of the scope of the present invention. Often parts of the carcasses can be saved even in an unhealthy carcass. It is believed that most processors would want to capture some of this possible product by providing inspectors to cut carcasses after an initial condemnation decision by the machine at inspection station A. It is quite possible, however, that some processors may decide to destroy all carcasses on side track 31 and not use an inspector B.

Figure 6:
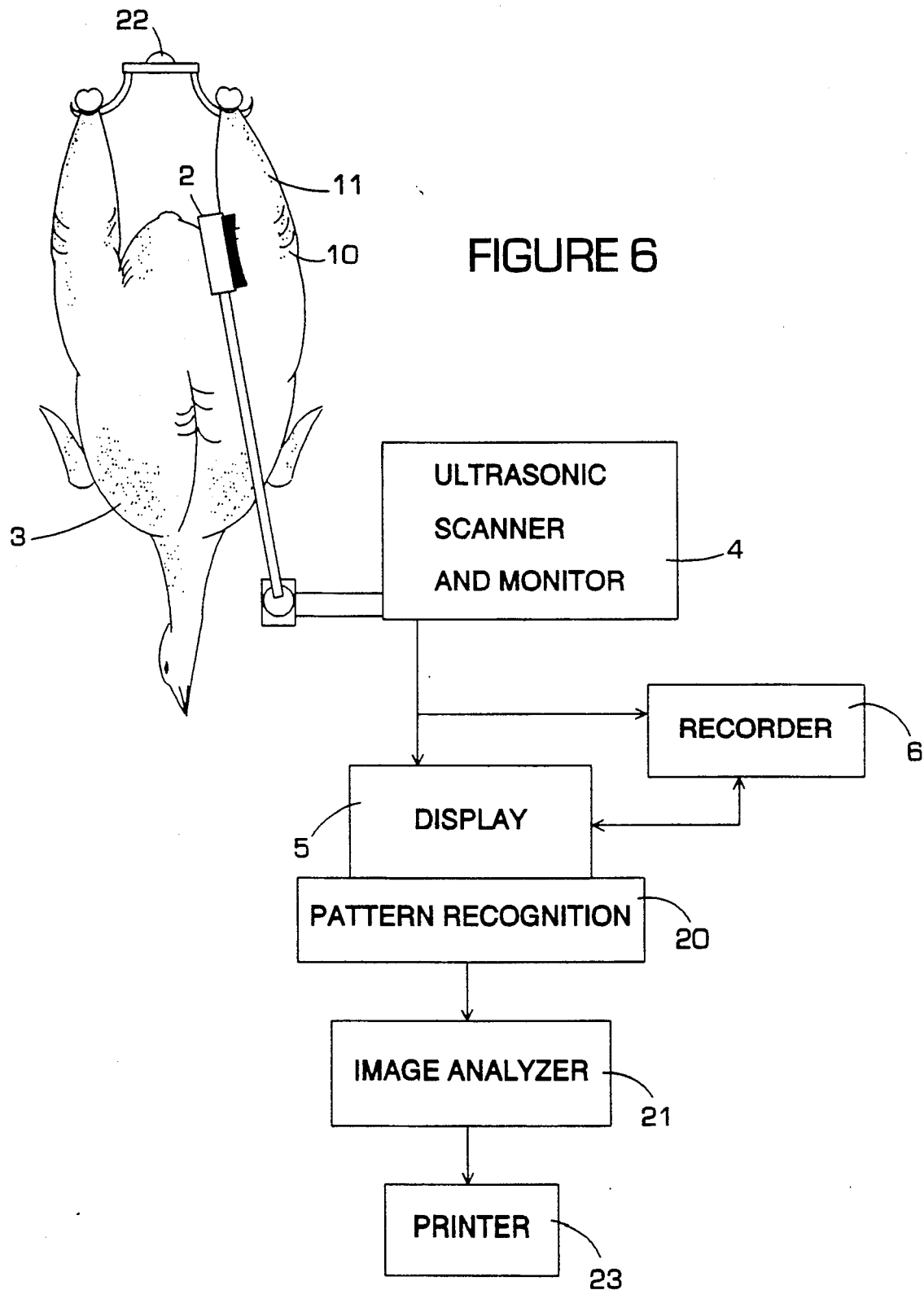
FIG. 6 is a perspective view of one possible embodiment of an automated ultrasound inspection station positioning an ultrasonic probe on a poultry carcass.

FIG. 6 shows and automated inspection station in greater detail. As shown, the probe 2 is mounted on a spring loaded base 35 such that the probe engages the tissue surrounding the tibia-femur joint 10. The pattern recognition equipment 20 and image analyzer 21 could recognize the osteomyelitis condition automatically. A condemnation condition could be shown by the activation of a light 22. This system could be used to examine every carcass 3. The probe 2 creates images fast enough such that the carcasses 3 could move along at a faster rate than would be possible by manual examination, thereby decreasing processing time.

The method of determining a bone deformation condition in an animal taught by the present invention includes positioning an ultrasonic probe on the animal such that a cross-sectional image is shown which includes an outline of a portion of bone to be examined. The image of the bone outline is compared with a norm reference image of a bone outline for a healthy animal and at least one known deformation pattern of images of bone outlines for animals requiring condemnation. The animal is condemned if the image has a greater correlation with one of the known deformation patterns than with the norm reference pattern.

Also taught hereinabove, is a method of developing a test for determining a condemnation condition in an animal. The method includes selecting a group of healthy animals, a group of animals known to have conditions requiring condemnation, a group of animals of unknown health. An ultrasound machine is used to create a series of cross-sectional images of the group of healthy animals. A norm reference pattern is determined for each cross-sectional image position by pooling information from the series of cross-sectional images of the group of healthy animals. The ultrasound machine is used to create a series of cross-sectional images of the group of animals known to have a condemnation condition and a condemnation condition reference pattern is determined for each cross-sectional image position by pooling information. The norm reference patterns and the condemnation condition reference patterns are compared at each cross-sectional image position. Each cross-sectional image position which shows a difference between the reference patterns is identified and the difference is used the ultrasound machine to sort the group of animals of unknown condition. Any animals showing the difference particular to the condemnation condition pattern are placed into a group of suspected condemnation condition animals for each cross-sectional image position showing the difference and all others animals are placed into a suspected healthy animal group. The accuracy of the sorting determination is confirmed by testing the group of suspected condemnation condition animals and the group of suspected healthy animals for the condemnation condition by known accepted techniques for each cross-sectional image position group showing the difference. The cross-sectional image positions showing differences with the greatest accuracy of sorting condemnation condition animals from healthy animals are selected for use as a condemnation test procedure.

The foregoing description has been directed to particular embodiments of the invention in accordance with the requirements of the Patent Statutes for the purposes of illustration and explanation. It will be apparent, however, to those skilled in this art that many modifications and changes will be possible without departure from the scope and spirit of the invention. It is intended that the following claims be interpreted to embrace all such modifications.

We claim:

1. A method of determining an abnormality or condemnation condition in an animal or carcass intended for human consumption, comprising:
    a) providing an ultrasound machine, including a probe for transmitting and receiving ultrasound signals such that said machine is capable of producing a cross-sectional image of an area to be examined;
    b) positioning said probe on said animal such that said cross-sectional image of said portion of the animal to be examined is shown;
    c) comparing said image of said portion of the animal being examined with a norm reference for a healthy animal and at least one known deformation pattern for tissue for animals requiring condemnation;
    d) condemning said animal if said image is more similar to one of said known deformation patterns than to said norm reference pattern.

2. The method of claim 1 wherein a correlation and said comparison are performed by an image analyzer and pattern recognition equipment modified to recognize said known deformation patterns such that said condemnation decision is made automatically by a machine.

3. The method of claim 1 wherein said animal or carcass is poultry and said known deformation pattern is a deformed medial condyle indicating osteomyelitis.

4. The method of claim 1 wherein said animal or carcass has been infected by *Staphylococcal auerus, Esrichi coli* or other microorganisms causing osteomyelitis.

5. An apparatus for determining a condemnation condition in a post mortem animal intended for human consumption, comprising:
    a) an ultrasound machine, including a probe for transmitting and receiving ultrasound signals, wherein said probe is positioned on said animal such that a cross-sectional image of a portion of the animal to be examined is shown;
    b) pattern recognition equipment for determining and identifying a pattern of anatomically distinct tissue and bone formation of said animal shown on said image;

c) an image analyzer for comparing and correlating said pattern of tissue and bone formation with a norm reference for a healthy animal and at least one known deformation pattern for tissue of animals requiring condemnation;

d) means for indicating a condemnation condition for said animal if said pattern recognition equipment determines said pattern of tissue and bone formation of said animal being examined has a greater correlation with one of said known deformation patterns than with said norm reference pattern.

6. The apparatus of claim 5 wherein said animal is poultry and said known deformation pattern is a deformed medial condyle of said animal indicating osteomyelitis.

7. The apparatus of claim 6 wherein said animal has been infected by *Staphylococcal auerus* or *Esrichi coli*.

8. A method of determining a bone deformation condition in an animal or carcass intended for human consumption, comprising:

a) providing an ultrasound machine, including a probe for transmitting and receiving ultrasound signals such that said machine is capable of producing a cross-sectional image of an area to be examined;

b) positioning said probe on said animal or carcass such that said cross-sectional image of said portion of said animal or carcass to be examined is shown which includes an outline of a portion a bone to be examined;

c) comparing said image of the portion of said animal or carcass being examined with a norm reference image of a bone outline for a healthy animal and at least one known deformation pattern of images of bone outlines for animals which have bone deformations;

d) identifying said animal as having a bone deformation condition if said image is more similar to one of said known deformation patterns than to said norm reference pattern.

9. The method of claim 8 wherein a correlation and said comparison are performed by an image analyzer and pattern recognition equipment modified to recognize said known deformation patterns such that said identification decision is made automatically by a machine.

10. The method of claim 9 wherein said animal or carcass is poultry and said known deformation pattern is a deformed medial condyle of said animal or carcass indicating osteomyelitis.

11. The method of claim 10 wherein said animal or carcass has been infected by *Staphylococcal auerus* or *Esrichi coli*.

12. A method of developing a test for determining a condemnation condition in animals intended for human consumption, comprising:

a) providing an ultrasound machine, including a probe for transmitting and receiving ultrasound signals such that said machine is capable of producing a cross-sectional image of an area to be examined;

b) selecting a group of healthy animals;

c) selecting a group of animals known to have conditions requiring condemnation;

d) using said ultrasound machine to create a series of cross-sectional images of said group of healthy animals;

e) determining a norm reference pattern for each cross-sectional image position by pooling information from said series of cross-sectional images of said group of healthy animals;

f) using said ultrasound machine to create a series of cross-sectional images of said group of animals known to have a condemnation condition;

e) determining a condemnation condition reference pattern for each cross-sectional image position by pooling information from said series of cross-sectional images of said group of animals known to have a condemnation condition;

g) comparing said norm refernce patterns and said condemnation condition reference patterns for each cross-sectional image position and identifying each cross-sectional image position which is different in said reference patterns;

h) using said ultrasound machine to sort a group of animals of unknown condition by placing any animals showing said difference particular to said condemnation condition pattern into a group of suspected condemnation condition animals for each cross-sectional image position showing said difference and all others animals into a suspected healthy animal group;

i) confirming the accuracy of said sorting determination by testing said group of suspected condemnation condition animals and said group of suspected healthy animals by accepted techniques for each cross-sectional image position group showing said difference; and j) selecting said cross-sectional image positions showing differences with the greatest accuracy of sorting condemnation condition animals from healthy animals for use as a condemnation test procedure.

13. A method of determining a deformation pattern indicating osteomyelitis in an animal or carcass intended for human consumption, comprising:

a) providing an ultrasound machine, including a probe for transmitting and receiving ultrasound signals such that said machine is capable of producing a cross-sectional image of an area to be examined including the outline of the bone;

b) positioning said probe on said animal such that said cross-sectional image of said portion of the animal to be examined is shown; and c) comparing said image of said portion of the animal being examined with a norm reference for a healthy animal and at least one known deformation pattern for tissue for animals infected by *Staphylococcal auerus, Esrichi coli* or other microorganisms causing osteomyelitis requiring condemnation.

14. The method of claim 13 wherein said animal or carcass is poultry and said known deformation pattern is a deformed medial condyle of said animal or carcass indicating osteomyelitis.

* * * * *